US009316662B2

(12) United States Patent
Ishigami et al.

(10) Patent No.: US 9,316,662 B2
(45) Date of Patent: Apr. 19, 2016

(54) AUTOMATED ANALYZER AND MAINTENANCE METHOD FOR SAME

(75) Inventors: Ryohei Ishigami, Tokyo (JP); Toshihide Orihashi, Tokyo (JP); Goro Yoshida, Tokyo (JP); Kenichi Nishigaki, Tokyo (JP); Hideyuki Yanami, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 136 days.

(21) Appl. No.: 14/239,624

(22) PCT Filed: Aug. 6, 2012

(86) PCT No.: PCT/JP2012/069971
§ 371 (c)(1),
(2), (4) Date: Feb. 19, 2014

(87) PCT Pub. No.: WO2013/035471
PCT Pub. Date: Mar. 14, 2013

(65) Prior Publication Data
US 2014/0202828 A1    Jul. 24, 2014

(30) Foreign Application Priority Data
Sep. 9, 2011  (JP) .................................. 2011-196609

(51) Int. Cl.
G01N 35/04 (2006.01)
G01N 21/78 (2006.01)
(Continued)

(52) U.S. Cl.
CPC ...... G01N 35/1009 (2013.01); G01N 35/00584 (2013.01); G01N 35/04 (2013.01); *G01N 21/251* (2013.01); *G01N 21/253* (2013.01); *G01N 21/78* (2013.01); *G01N 2035/00316* (2013.01)

(58) Field of Classification Search
CPC .............. G01N 35/1009; G01N 35/04; G01N 35/00584; G01N 21/251; G01N 21/253; G01N 21/78; G01N 2035/00316

USPC ......................... 422/63–67; 198/860.3–860.5
See application file for complete search history.

(56) References Cited

U.S. PATENT DOCUMENTS 5,827,479 A   10/1998   Yamazaki et al.
6,456,365 B1   9/2002   Hosaka et al.
(Continued)

FOREIGN PATENT DOCUMENTS

JP    07-159414 A    6/1995
JP    09-196925 A    7/1997
(Continued)

OTHER PUBLICATIONS

Extended European Search Report received in corresponding European Application No. 12829714.0 dated Mar. 10, 2015.
(Continued)

*Primary Examiner* — Mark A Deuble
(74) *Attorney, Agent, or Firm* — Mattingly & Malur, PC

(57) ABSTRACT

An automated analyzer includes a conveyance mechanism to convey a specimen, an analysis portion to analyze the specimen, and a device cover to cover a movable mechanism including the conveyance mechanism. The automated analyzer is provided with an interlock mechanism and an interlock release mechanism. The interlock mechanism stops an operation of the movable mechanism when the device cover is opened. The interlock release mechanism disables all or part of the interlock mechanism. The interlock mechanism is enabled when a lever 301 is in contact with a safety switch 302. The interlock mechanism is disabled or partially disabled when the lever 301 is not in contact with the safety switch 302. This enables to prevent a user from inadvertently touching the movable mechanism including a hazard region during analysis of the automated analyzer or a maintenance task. Only a specific maintenance task can be performed with the device cover opened.

17 Claims, 14 Drawing Sheets

(51) Int. Cl.
*G01N 35/10* (2006.01)
*G01N 21/25* (2006.01)
*G01N 35/00* (2006.01)

(56) References Cited

U.S. PATENT DOCUMENTS

| | | | |
|---|---|---|---|
| 6,589,789 B1 | 7/2003 | Hubert et al. | |
| 2003/0092186 A1* | 5/2003 | Pressman | B01D 61/18 436/46 |
| 2005/0130453 A1 | 6/2005 | Inada et al. | |
| 2005/0175503 A1* | 8/2005 | Shiba | G01N 35/00663 422/64 |
| 2005/0279281 A1 | 12/2005 | Yamashita et al. | |
| 2007/0217951 A1* | 9/2007 | Matsumoto | B01F 11/0002 422/67 |
| 2008/0011106 A1* | 1/2008 | Kitagawa | G01N 35/025 73/863 |
| 2009/0180931 A1* | 7/2009 | Silbert | G01N 35/0099 422/63 |
| 2010/0284777 A1 | 11/2010 | Xiao et al. | |

FOREIGN PATENT DOCUMENTS

| | | |
|---|---|---|
| JP | 10-048195 A | 2/1998 |
| JP | 2000-64676 A | 2/2000 |
| JP | 2001-126976 A | 5/2001 |
| JP | 2001-237163 A | 8/2001 |
| JP | 2002-098659 A | 4/2002 |
| JP | 2003-262642 A | 9/2003 |
| JP | 2006-012912 A | 1/2006 |
| JP | 3141576 U | 4/2008 |
| JP | 2008-216173 A | 9/2008 |
| JP | 2009-190103 A | 8/2009 |

OTHER PUBLICATIONS

Japanese Office Action received in corresponding Japanese Application No. 2013-532501 dated Jun. 30, 2015.

\* cited by examiner

FIG. 5

| No. | MAINTENANCE NAME | DATE |
|---|---|---|
| 1 | RESET | |
| 2 | RACK STORAGE | |
| 3 | AIR PURGE | |
| 4 | CELL DETERGENT PRIME OPERATION | |
| 5 | DILUTED SOLUTION PRIME OPERATION | |
| 6 | ISE REAGENT PRIME OPERATION | |
| 7 | PHOTOMETER CHECK | |
| 8 | CELL PLAQUE MEASUREMENT | |
| 9 | ISE CHECK | |
| 10 | ⚒ REACTION TANK WATER REPLACEMENT | |
| 11 | ⚒ DILUTION CELL CLEANING | |
| 12 | ⚒ REACTION CELL CLEANING | |
| 13 | ⚒ REAGENT FLOW CHANNEL CLEANING | |
| 14 | | |
| 15 | ⚒ REACTION TANK CLEANING | |
| 16 | | |
| 17 | | |
| 18 | 🗄 DILUTION CELL REPLACEMENT | |
| 19 | 🗄 REACTION CELL REPLACEMENT | |
| 20 | 🗄 LIGHT SOURCE LAMP REPLACEMENT | |

501 points to rows 10-15; 502 points to row 19.

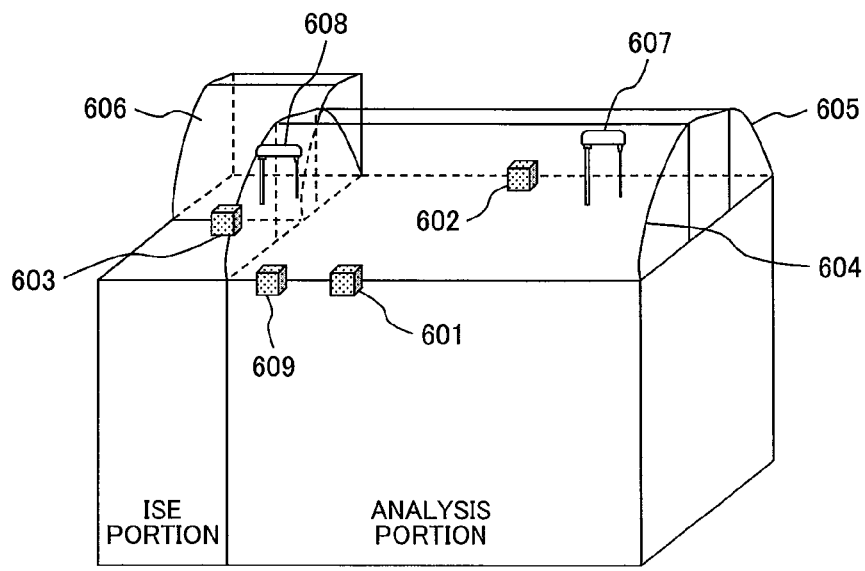

FIG. 6

FIG. 8E
PERFORM ISE REAGENT PRIME PROCESS
AFTER RESET OPERATION IS COMPLETE
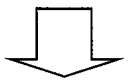
RESET OPERATION AND ISE REAGENT PRIME PROCESS
CAN BE ASSUMED DISCRETE MAINTENANCE ITEMS
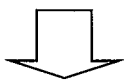
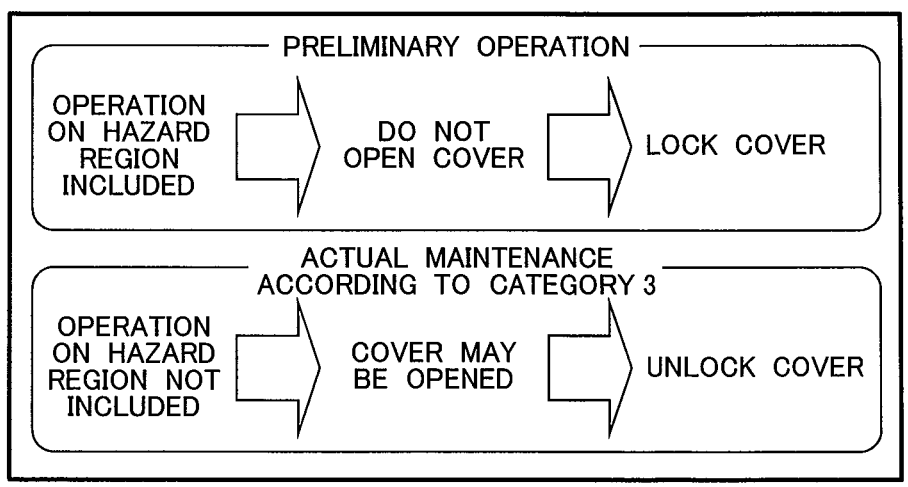

AUTOMATED ANALYZER AND MAINTENANCE METHOD FOR SAME

TECHNICAL FIELD

The present invention relates to an automated analyzer and its maintenance method to analyze blood, etc. biochemically and immunologically.

BACKGROUND ART

An automated analyzer to analyze specimens such as blood effectively uses an interlock function to control opening and closing of a cover in order to prevent a user from touching a hazardous portion during analysis or maintenance operation. However, some maintenance tasks need to be performed while the mechanism operates with the cover opened for the purpose of visual confirmation or internal cleaning. The interlock mechanism needs to satisfy demands for this situation.

Patent literature 1 discloses the automated analyzer having a function to stop operation of a dispensing mechanism and release the state of a cover closed by a lock mechanism.

CITATION LIST

Patent Literature

PTL 1: Japanese Patent Application Laid-Open No. 2008-216173

SUMMARY OF INVENTION

Problems to be Resolved by the Invention

An automated analyzer needs to prevent a user from inadvertently touching a mechanism portion including hazardous parts during analysis operation or maintenance task. One solution is requested to provide an interlock mechanism that allows the mechanism portion to operate only when a device cover is closed. The interlock is recommended to physically turn off the power, not electronically. However, the user may inadvertently stop the analysis operation if opening the cover turns off the power simply based on requirements of the safety standard. Therefore, the interlock is recommended to be capable of allowing a device to issue the timing to open the cover without problem.

Some maintenance tasks need to be performed while the mechanism portion operates with the cover opened for the purpose of visual confirmation or internal cleaning. Accordingly, the interlock mechanism needs to include a function to operate part of the mechanism portion with the device cover opened and enable specific maintenance tasks in addition to the function to operate the mechanism portion only when the device cover is closed. The safety standard requires notifying the user of a hazardous condition when the interlock is partially disabled.

It is an object of the present invention to provide an automated analyzer including an interlock mechanism capable of ensuring safety and usability.

Means for Solving the Problems

The automated analyzer according to the invention is provided with an interlock mechanism and an interlock release mechanism. The interlock mechanism stops operation of the movable mechanism when the device cover is opened. The interlock release mechanism disables all or part of the interlock mechanism.

Advantageous Effect of the Invention

The invention can prevent a user from inadvertently touching the movable mechanism including a hazard region during analysis of the automated analyzer or a maintenance task.

Further, the invention can perform only a specific maintenance task with the device cover opened.

BRIEF DESCRIPTION OF DRAWINGS

FIG. 5 is a display screen as an example of a maintenance menu.

FIG. 6 is a perspective view illustrating a schematic configuration of the interlock mechanism.

FIG. 8E illustrates an effect of an ISE reagent prime process as an example of category 3.

DESCRIPTION OF EMBODIMENTS

Figure 1:
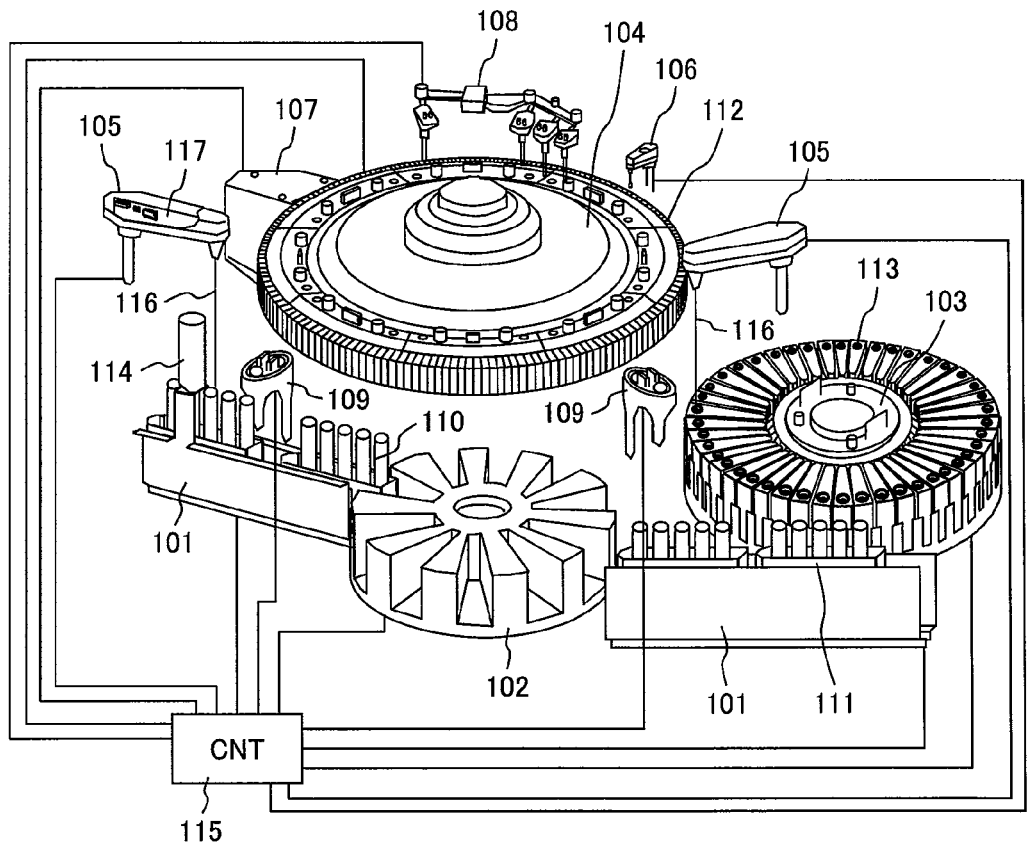
FIG. 1 is a perspective view illustrating an automated analyzer.

The present invention relates to an automated analyzer to analyze blood, etc. biochemically and immunologically. More particularly, the invention relates to an interlock mechanism to control opening and closing of a device cover.

The invention locks the device cover and prevents contact by a user so that the user does not inadvertently open the device cover during analysis operation or maintenance task for the automated analyzer. The automated analyzer according to the invention includes an interlock mechanism to stop supplying the power to a movable mechanism and prevent its operation if the device cover opens. Further, the automated analyzer according to the invention includes an interlock release mechanism to supply the power to the movable mechanism and enable only a specific maintenance task when a maintenance key etc. is inserted into the interlock mechanism with the device cover opened to enable maintenance mode. Moreover, the automated analyzer according to the invention includes a manipulation screen corresponding to an interlock mechanism state. The manipulation screen displays restrictions on an available maintenance task.

The following describes the automated analyzer and its maintenance method according to an embodiment of the invention.

The automated analyzer includes a conveyance mechanism, an analysis portion, and device cover. The conveyance mechanism conveys specimens. The analysis portion analyzes specimens. The device cover covers a movable mechanism including the conveyance mechanism. The automated analyzer further includes an interlock mechanism and an interlock release mechanism. The interlock mechanism stops operation of the movable mechanism when the device cover is opened. The interlock release mechanism partially or totally disables the interlock mechanism.

In the automated analyzer, the interlock release mechanism is recommended to disable the interlock mechanism to enable operation of the movable mechanism with the device cover opened and enables a specific maintenance task that is disabled by the interlock mechanism for the user.

The automated analyzer is recommended to include a display portion to visually notify the user that the device cover is opened and the movable mechanism is inoperative and that the device cover is opened but only a specific maintenance task is available.

In the automated analyzer, the display portion is recommended to display restrictions on an available maintenance task depending on whether the interlock mechanism is enabled, disabled, or partially disabled. In addition, the display portion preferably displays a maintenance task available only in a state of activating a maintenance tool to notify the user that the safety needs to be ensured.

The automated analyzer is recommended to partially or totally disable the interlock mechanism only at permitted timing. The "permitted timing" signifies the timing at which the movable mechanism operates to necessitate opening the cover. An example case is to visually confirm the position of the movable mechanism up-close.

The automated analyzer is recommended to inhibit opening of the device cover only when the movable mechanism operates. The automated analyzer is recommended to allow opening of the device cover and to enable a specific maintenance task without disabling the interlock mechanism when the movable mechanism does not operate.

According to the maintenance method for the automated analyzer, the interlock mechanism stops operation of the movable mechanism when the device cover is opened. The interlock release mechanism partially or totally disables the interlock mechanism.

According to the maintenance method for the automated analyzer, the interlock release mechanism is recommended to disable the interlock mechanism and enable operation of the movable mechanism while the device cover is opened. The interlock release mechanism is recommended to enable a specific maintenance task the interlock mechanism disabled for the user.

The maintenance method for the automated analyzer is recommended to visually notify the user that the movable mechanism is inoperative with the device cover opened and that only a specific maintenance task is available with the device cover opened.

The maintenance method for the automated analyzer is recommended to display restrictions on an available maintenance task corresponding to a state of enabling, disabling, or partially disabling the interlock mechanism and to display a maintenance task only available in a state of activating a maintenance tool for the user to recognize the necessity of ensuring safety.

The maintenance method for the automated analyzer is recommended to partially or totally disable the interlock mechanism at permitted timing.

The maintenance method for the automated analyzer is recommended to inhibit the device cover from opening only when the movable mechanism operates. The maintenance method for the automated analyzer is recommended to allow the device cover to open and to enable a specific maintenance task without disabling the interlock mechanism when the movable mechanism does not operate.

The automated analyzer is recommended to further include a maintenance switch. The automated analyzer is recommended to lock the device cover when the device cover is closed and the maintenance switch opens a contact after reception of a request to perform maintenance. The automated analyzer is recommended to perform a preparatory operation for maintenance with the device cover locked, unlock the device cover thereafter, enable operation of the movable mechanism with the device cover opened, and perform maintenance subsequent to the preparatory operation.

The automated analyzer is recommended to further include a maintenance switch and a maintenance key. The automated analyzer is recommended to lock the device cover when the device cover is closed after reception of a request to perform maintenance. The automated analyzer is recommended to perform a preparatory operation for maintenance with the device cover locked, unlock the device cover thereafter, and provide an option whether to open the device cover. The automated analyzer is recommended to display an instruction to open the device cover and rotate the maintenance key when an option to open the device cover is selected and the maintenance switch opens a contact. It is recommended to confirm that the maintenance switch closes the contact, then enable operation of the movable mechanism with the device cover opened, and perform maintenance subsequent to the preparatory operation.

Embodiments exemplifying the present invention will be described with reference to the accompanying drawings.

Example 1

FIG. 1 is a schematic configuration diagram illustrating an example of the automated analyzer according to the invention.

As illustrated in FIG. 1, the automated analyzer includes a conveyance line 101, a rotor 102, a reagent disk 103, a reaction disk 104, a dispensing mechanism 105, a stirring mechanism 106, a spectroscope 107, a reaction container cleaning mechanism 108, a nozzle cleaning mechanism 109, and a control unit 115.

A specimen rack 111 holds a specimen container 110 that contains a specimen. The dispensing mechanism 105 conveys a necessary amount of reagent to a reaction container 112 to perform colorimetric analysis using biochemical reaction. The conveyance line 101 conveys the specimen rack 111 to a position where the dispensing mechanism 105 is capable of dispensing operation. The conveyance line 101 is further connected to the rotor 102. Rotating the rotor 102 interchanges the specimen rack 111 between one conveyance line 101 and another.

The reagent disk 103 holds a reagent container 113 containing a reagent that reacts on components in a specimen to be analyzed. The dispensing mechanism 105 needs to transport as much reagent as needed for the colorimetric analysis to the reaction container 112. For this purpose, the reagent disk 103 rotatively transports the reagent container 113 to a position where the dispensing mechanism 105 is capable of dispensing operation.

While the reagent acts on components in the specimen over a homeothermal medium such as water, the reaction disk 104 holds the reaction container 112 containing a reaction solution as a mixture of the specimen and the reagent. The reaction disk 104 rotatively transports the reaction container 112 to positions corresponding to operations of the spectroscope 107, the stirring mechanism 106, and the reaction container cleaning mechanism 108 that perform colorimetric analysis.

During the colorimetric analysis, the dispensing mechanism 105 suctions a necessary amount of reagent corresponding to the specimen and the analysis target from the specimen container 110 or the reagent container 113. The dispensing mechanism 105 discharges the suctioned reagent into the reaction container 112.

The dispensing mechanism 105 is provided with a nozzle 116 that is connected to a fluid level sensor 117 to detect the presence or absence of liquid based on changes in the electrostatic capacity. A shield portion 114 is provided near a position for the dispensing operation.

The specimen is discharged into the reaction container 112 from the specimen container 110. The reagent is discharged into the reaction container 112 from the reagent container 113. The stirring mechanism 106 stirs the reaction solution in the reaction container 112 to accelerate reaction between components to be analyzed in the specimen and the reagent. The spectroscope 107 uses the absorbance measurement to perform colorimetric analysis on the reaction solution that is stirred by the stirring mechanism 106 and is chemically reacted.

The reaction container cleaning mechanism 108 suctions the reaction solution from the reaction container 112 that has completed the colorimetric analysis. The reaction container cleaning mechanism 108 discharges detergent to clean the reaction container 112.

The dispensing mechanism 105 has discharged the specimen and the reagent. The nozzle cleaning mechanism 109 cleans a nozzle tip of the dispensing mechanism 105 so that residues do not affect the next analysis target.

An overview of the interlock function will be described.

The interlock function is provided for a device top cover (also referred to as a device cover) to prevent a user from inadvertently touching the mechanism portion during operation such as analysis and maintenance. That is, the device cover is provided for safety of users. When the device cover is opened, the interlock function stops supplying 24 V DC (direct current 24 V) as a power supply for movable mechanism portions (mainly a motor and a solenoid valve). The interlock function uses the hardware to stop mechanism operation.

One automated analyzer may include multiple device covers.

Figure 2:
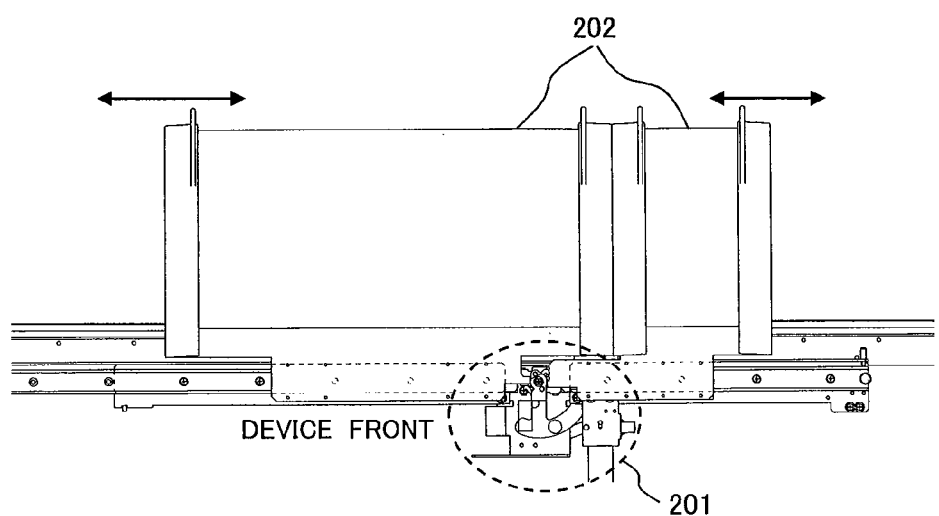
FIG. 2 is a front view illustrating a schematic configuration of an interlock mechanism.

FIG. 2 illustrates a top cover for the analysis portion as an example of the device cover.

The top cover 202 is connected to the interlock mechanism 201. Opening the top cover 202 operates the interlock mechanism 201 to stop supplying the power.

Figure 3A:
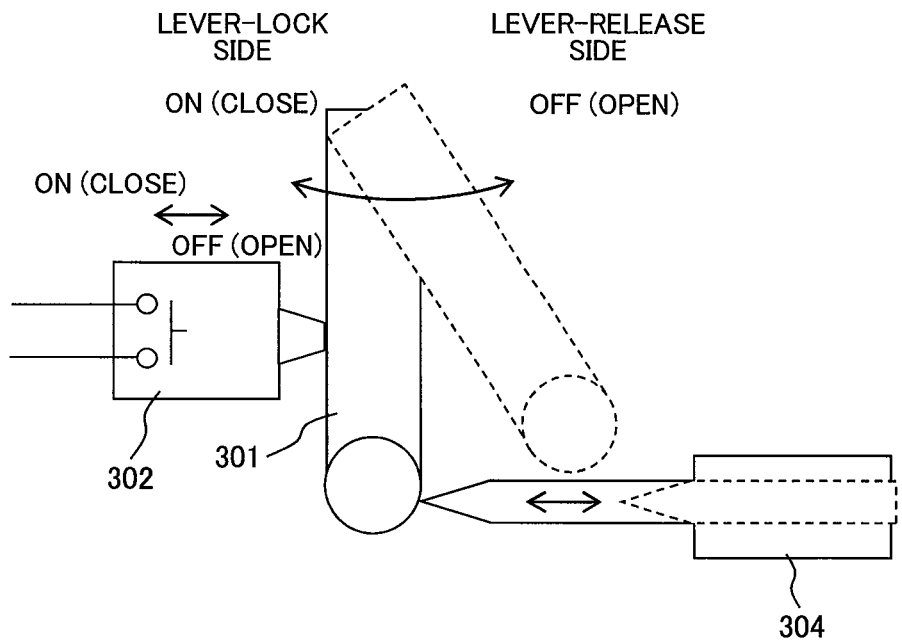
FIG. 3A is a schematic diagram illustrating a configuration of an interlock mechanism according to an example.

FIG. 3A illustrates the interlock mechanism in detail. Table 1 lists component specifications.

TABLE 1

| | Component | Specification |
| --- | --- | --- |
| 301 | Lever | Determines the release or lock state. |
| 302 | Safety switch | Turns on or off a contact. |
| 303 | Maintenance key | Changes the device to maintenance mode. Rotating the maintenance key closes the safety switch 302. |
| 304 | Solenoid | Locks the lever 301. |

A lever 301 is also referred to as an interlock lever or a cover opening/closing lever. Moving the lever 301 from the lock position to the release position enables the top cover to open. FIG. 3A uses a broken line to indicate the release position of the lever 301.

Moving the lever 301 to the release position turns off the safety switch 302 in terms of hardware to stop supplying 24 V DC as the power for each motor. The top cover is assumed open when the lever 301 is set to the release position. According to the interlock lever mechanism (interlock mechanism), the lock mechanism of the solenoid 304 allows the lever 301 to move when the device power supply turns off or supplying 24 V to the solenoid 304 stops. The safety switch 302 attached to the device cover turns off to open the contact, that is, totally or partially disable the interlock mechanism when the lever 301 is moved to the release position (allowing no contact between the lever 301 and the safety switch 302). As illustrated in FIG. 3A, placing the lever 301 in contact with the safety switch 302 turns on the safety switch 302 (to close the contact and enable the interlock mechanism).

Figure 3B:
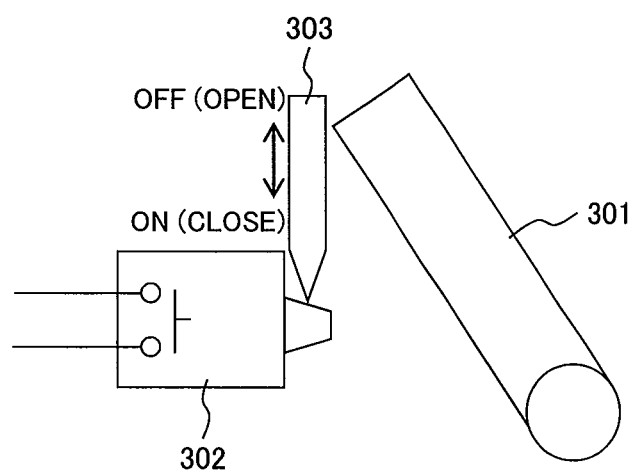
FIG. 3B is a schematic diagram illustrating the configuration of the interlock mechanism when a maintenance key is inserted.

The maintenance key 303 illustrated in FIG. 3B will be described with reference to the maintenance mode.

Various states will be defined as follows.

In lever lock mode, the solenoid 304 in FIG. 3A pushes the lever 301 and fastens it at the lock position. The lever lock mode drives the solenoid 304 under software control to lock the lever 301 during initialization, test maintenance (hereinafter abbreviated to T/M), and operation (to operate the mechanism).

Lever lock release mode unlocks the lever 301 under software control and allows the lever 301 to move to the release position. In this state, moving the lever 301 to the release position stops supplying the 24 V power to the motor in terms of hardware. Transition to the standby state automatically unlocks the lever 301 under software control.

In maintenance mode, while the cover is opened, connecting the maintenance key 303 supplies 24 V to the motor in terms of hardware and enables restricted T/M to perform. The maintenance key 303 functions as a tool for the user to recognize danger (need to ensure safety). The maintenance key 303 is an example of such tool. The maintenance key 303 need not be used if the user can recognize the need to ensure safety. For example, a system may provide a switch for a portion the user always continues to touch during a maintenance task. The maintenance key 303 and such a system are generically referred to as a "maintenance tool."

The use of the maintenance key enables the maintenance mode when the lever lock is released and the top cover is opened. The maintenance mode monitors a voltage of 24 V DC and a driver board fuse similarly to the normal standby state (top cover closed). The monitor starts one second after transition to the maintenance mode, for example. The maintenance mode needs to inform the user that no safety is ensured. Therefore, the maintenance mode allows the maintenance key 303 to be inserted only when the top cover is opened. In other words, the maintenance mode prevents the cover from closing or the lever from locking when the maintenance key 303 is connected.

A device administrator needs to strictly manage the maintenance key 303.

Figure 4:
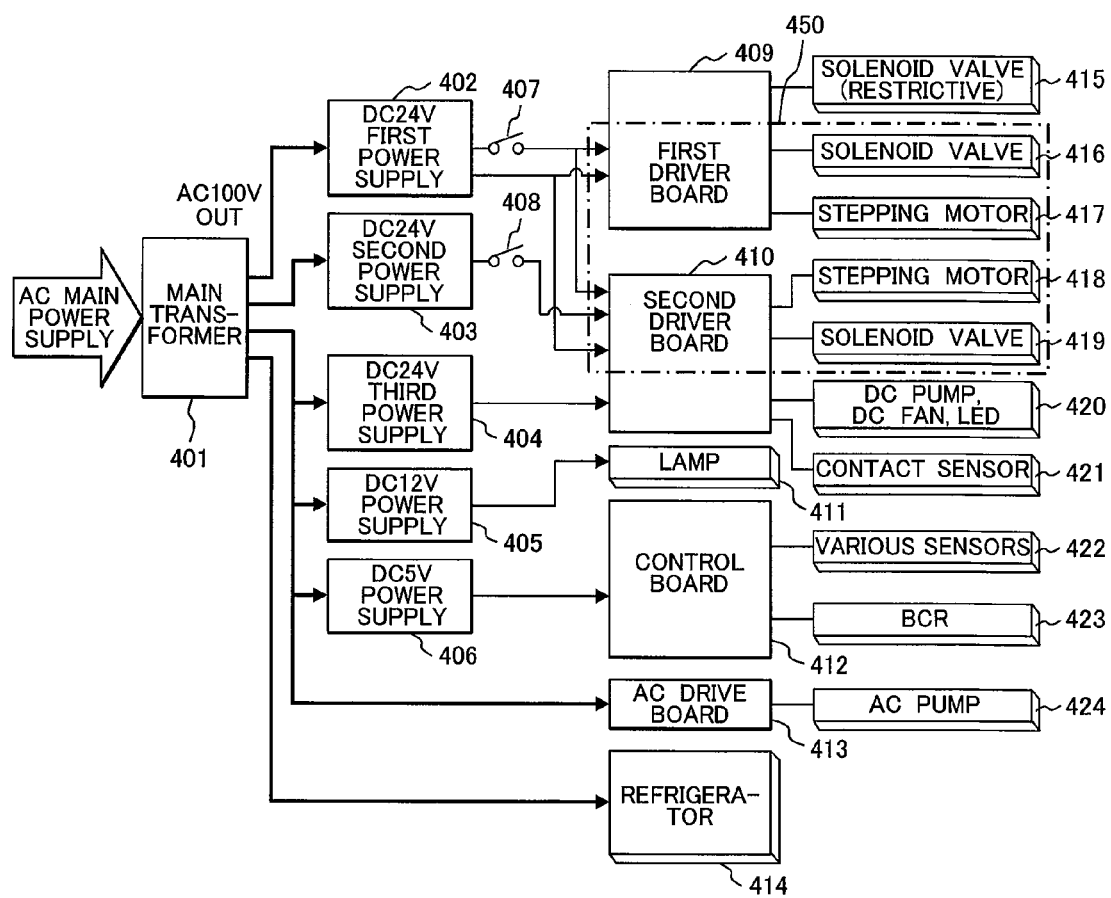
FIG. 4 is a block diagram illustrating a configuration of a power supply system in the automated analyzer.

FIG. 4 illustrates a power supply system.

As illustrated in FIG. 4, the power supply system includes a main transformer 401, a 24 V DC first power supply 402, a 24 V DC second power supply 403, a 24 V DC third power supply 404, a 12 V DC power supply 405, a 5 V DC power supply 406, a DC first power relay 407, a DC second power relay 408, a first driver board 409, a second driver board 410, a lamp 411, a control board 412, an AC drive board 413, a refrigerator 414, solenoid valves 415 and 416, stepping motors 417 and 418, a solenoid valve 419, a DC pump 420 (including a DC pump, a DC fan and LED), a contact sensor 421, various sensors 422, a BCR 423 (bar code reader), and an AC pump 424. An interlock control target 450 corresponds to an area enclosed in the dash-dot line. That is, the interlock control target 450 contains the solenoid valve 416 and the stepping motor 417 connected to the first driver board 409 and the stepping motor 418 and the solenoid valve 419 connected to the second driver board 410. In the specification, "DC" signifies direct current and "AC" signifies alternate current.

Turning off the safety switch 302 in FIG. 3A turns off the DC first power relay 407 and the DC second power relay 408 (also collectively referred to as a "24 V DC power relay") in FIG. 4. Turning off the safety switch 302 entirely (however with some exceptions) stops outputting 24 V DC to the first driver board 409 and the second driver board 410 (also collectively referred to as a "driver board") in FIG. 4. The driver board uses the 24 V DC to control the drive of the stepping motors 417 and 418 and operation to open and close the solenoid valves 415, 416, and 419. The interlock operation disables operation of all the stepping motors 417 and 418 and the solenoid valves 416 and 419 (however with some exceptions) in the analysis portion.

In this case, a related system on the driver board is detected as fused even if it is not actually fused. The second driver board 410 connects with a DC pump, a DC fan, and a switch contact monitoring circuit that need to be controlled even during interlock operation. These components are supplied with the power of 24 V DC for a different system not contained in the interlock control target 450. Accordingly, it is possible to monitor the drive of a circulation pump and various device states even during the interlock operation.

The software monitor control will be described.

First, the following describes a case of opening the top cover in the standby state.

Opening the top cover (that is, releasing the lever) is assumed to be the standby state. In this case, the screen displays information to distinguish that standby state from a standby state of supplying 24 V. An attempt may be made to start an unspecified maintenance operation including operations and initialization. In such a case, the screen outputs an alarm notifying that the maintenance operation cannot start because the cover is opened. Device states are monitored according to four types of detection situations such as detecting a cover opening sensor, a safety switch contact, driver board fuse blowing, and the maintenance key.

The following then describes transition from the state of opening the top cover to the maintenance mode.

When the top cover is opened, the use of the maintenance key resumes the 24 V DC power supply, detects the top cover to be open, and does not detect blowing of both fuses on the driver boards. The automated analyzer confirms the maintenance key detection and transitions to the maintenance mode.

Thereafter, the screen displays information so that the user can recognize the maintenance mode. Available maintenance is limited.

As illustrated in FIG. 5, maintenance items are marked on the screen (display portion) so that the user can confirm whether the maintenance items are available. In FIG. 5, a maintenance mode symbol 501 indicates that the maintenance item is available only in the maintenance mode. A lever lock release mode symbol 502 indicates that the maintenance item is available only in the lever lock release mode.

Finally, the restoration will be described.

The automated analyzer completes transition to the lever lock mode at the time to start the next maintenance or operation with the lock lever closed. When starting the T/M or operation, the automated analyzer checks detection states on each sensor and device states. If needed, the automated analyzer locks the lever using the solenoid and proceeds to the reset operation.

Example 2

The automated analyzer is configured similarly to that illustrated in FIG. 1.

An overview of the interlock function will be described.

The device cover has the interlock function to prevent the user from inadvertently touching the mechanism portion during operation (analysis and maintenance). The interlock function is provided for device covers such as an analysis portion front cover, an analysis portion rear cover, and an ISE (Ion Selective Electrodes) portion cover. When any of the analysis portion front cover, the analysis portion rear cover, and the ISE portion cover is opened, the interlock function stops supplying the power to the movable mechanism portion (motor) and stops mechanism operation in terms of hardware.

FIG. 6 is a perspective view illustrating the schematic configuration of the interlock mechanism.

As illustrated in FIG. 6, an analysis portion front cover 604, an analysis portion front cover 605, and an ISE portion cover 606 are connected to an analysis portion front interlock mechanism 601, an analysis portion rear interlock mechanism 602, and an ISE portion interlock mechanism 603, respectively. These interlock mechanisms are collectively referred to as the interlock mechanism. In FIG. 6, the analysis portion front cover 604, the analysis portion front cover 605, and the ISE portion cover 606 are provided as device covers. The interlock mechanism is provided for each cover to protect the user against an analysis portion hazard region 607 and an ISE portion hazard region 608.

A maintenance key 609 will be described with reference to the maintenance mode later.

Figure 7A:
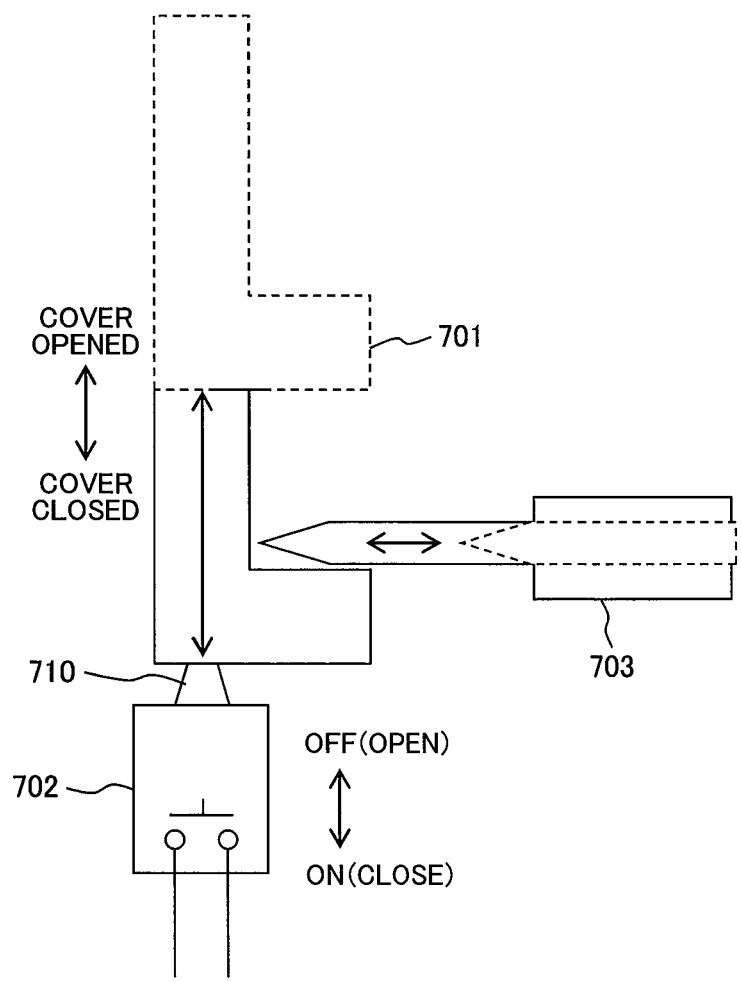
FIG. 7A is a schematic diagram illustrating a configuration of an interlock mechanism according to another example.
Figure 7B:
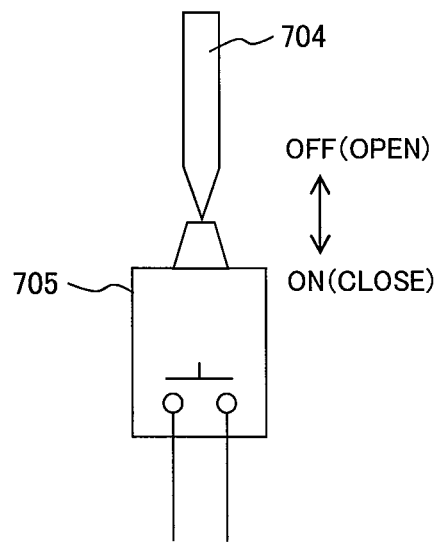
FIG. 7B is a schematic diagram illustrating the configuration of the interlock mechanism when a maintenance key is inserted.

FIGS. 7A and 7B illustrate examples of the interlock mechanism. Table 2 lists component specifications.

TABLE 2

| | Component | Specification |
|---|---|---|
| 701 | Device cover | Configured to be lockable using a solenoid. |
| 702 | Safety switch | Turns on or off a contact. |
| 703 | Solenoid | Locks the device cover not to open. |
| 704 | Maintenance key | Changes the device to maintenance mode. Rotating the maintenance key closes the maintenance switch 705. |
| 705 | Maintenance switch | Turns on or off a contact. |

Opening or closing the device cover 701 turns on or off the safety switch 702. The software monitors the on/off state of the safety switch 702. When the device cover 701 opens, the safety switch 702 turns off (to open the contact), stops supplying the power to the movable mechanism portion (motor), and stops mechanism operation in terms of hardware. When the device state results from a mechanism operation, the automated analyzer confirms closing of the device cover 701 using the software and allows the solenoid 703 to lock the device cover 701. As illustrated in FIG. 7A, the device cover 701 comes in contact with a contact 710 fixed to the safety switch 702 to turn on the safety switch 702.

Figure 7C:
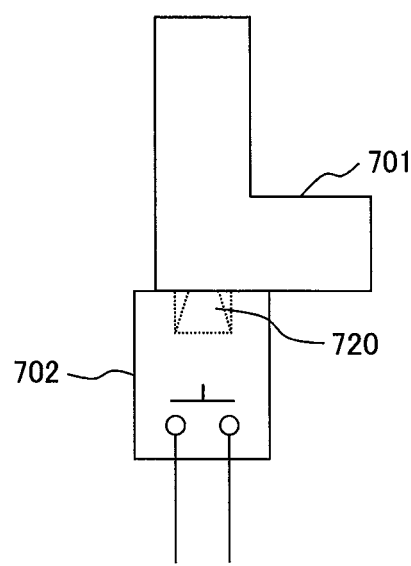
FIG. 7C is a schematic diagram illustrating a configuration of the interlock mechanism according to a modification.

In FIG. 7C, the safety switch 702 includes a movable contact 720. The device cover 701 pushes the contact 720 into the safety switch 702.

The maintenance key 704 and the maintenance switch 705 in FIG. 7B will be described with reference to the maintenance mode later.

Definitions of the states will be described.

In cover lock mode, the solenoid 703 pushes to lock the covers (the analysis portion front cover 604, the analysis portion front cover 605, and the ISE portion cover 606 in FIG. 6) so that the covers do not open. The automated analyzer drives the solenoid 703 under the software control to lock the lever during initialization, T/M, and operation (to operate the mechanism).

Cover lock release mode unlocks the cover under software control and enables the cover to open. In this state, opening the cover stops supplying the power to the motor in terms of hardware. Transition to the standby state automatically unlocks the lever 301 under software control.

In the maintenance mode, connecting the maintenance key 704 with the cover opened supplies the power to the motor in terms of hardware and enables restricted T/M to be performed. While any of the covers is opened, the use of the maintenance key 704 enables the maintenance mode. In the maintenance mode, the automated analyzer monitors voltages and driver board fuses similarly to the normal standby state (all covers closed). The monitoring starts one second after transition to the maintenance mode, for example. The maintenance mode needs to notify the user that no safety is ensured. While the maintenance key is connected, the maintenance mode disallows the initialization, the T/M and operations unavailable in the maintenance mode even if the cover is closed.

Categories of maintenance items will be described. Maintenance items are categorized to establish workflows according to the categories and simplify the system.

The maintenance includes many maintenance items to perform preparatory operations or post-operations such as mechanism reset as preparatory operations for the maintenance to be actually performed. The preparatory operation and the post-operation are defined as "preliminary operation." The maintenance to be actually performed is defined as "actual maintenance."

Table 3 lists preliminary operation, actual maintenance, the necessity to open the cover, and categories. Two bottom rows in the table provide meanings of ○ and x in the columns.

TABLE 3

| Preliminary operation | Actual maintenance | Necessity to open the cover | Category | Details |
|---|---|---|---|---|
| ○ | ○ | ○ | 1 | |
| ○ | ○ | x | 1 | |
| ○ | x | ○ | 4 | Also available as category 2 |
| ○ | x | x | 2 | |
| x | ○ | ○ | 3 | |
| x | ○ | x | 2 | |
| x | x | ○ | 4 | Also available as category 2 |
| x | x | x | 2 | |
| ○ Safe or none | ○ Safe | ○ Need or need not open the cover | | |
| x Hazardous | x Hazardous | x None | | |

Category 1 signifies T/M in which the preliminary operation and the actual maintenance do not accompany hazardous mechanism operation. Category 1 can ensure safety for the user. Therefore, category 1 is performed in the cover lock release mode.

Figure 8A:
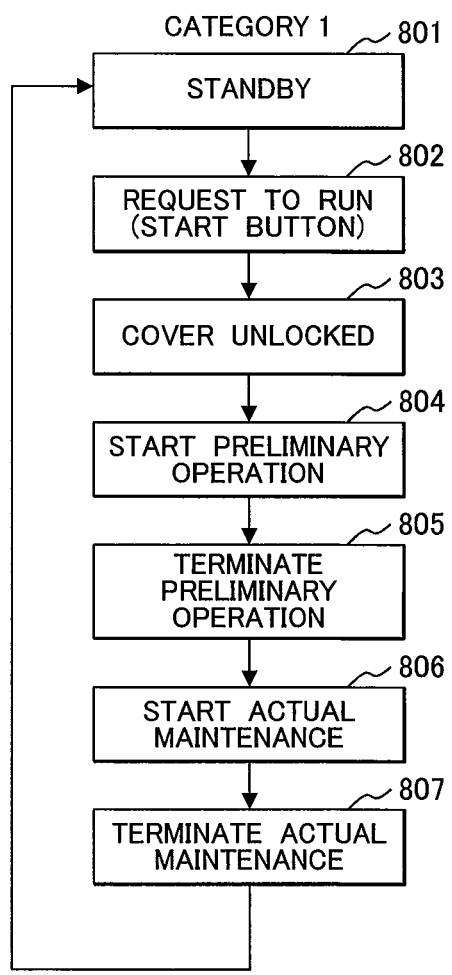
FIG. 8A illustrates a workflow of category 1.

FIG. 8A illustrates a workflow of category 1.

In FIG. 8A, pressing a request start button (802) in the standby state 801 enters a state of no cover lock 803. The preliminary operation starts (804). The preliminary operation terminates (805). Then, the actual maintenance starts (806). The actual maintenance terminates (807). Then, the standby state 801 is resumed.

Category 2 signifies T/M in which the preliminary operation or the actual maintenance accompanies hazardous mechanism operation. Category 2 is performed in the cover lock mode to ensure the user's safety. Category 2 applies to T/M items that do not need to open the cover.

Figure 8B:
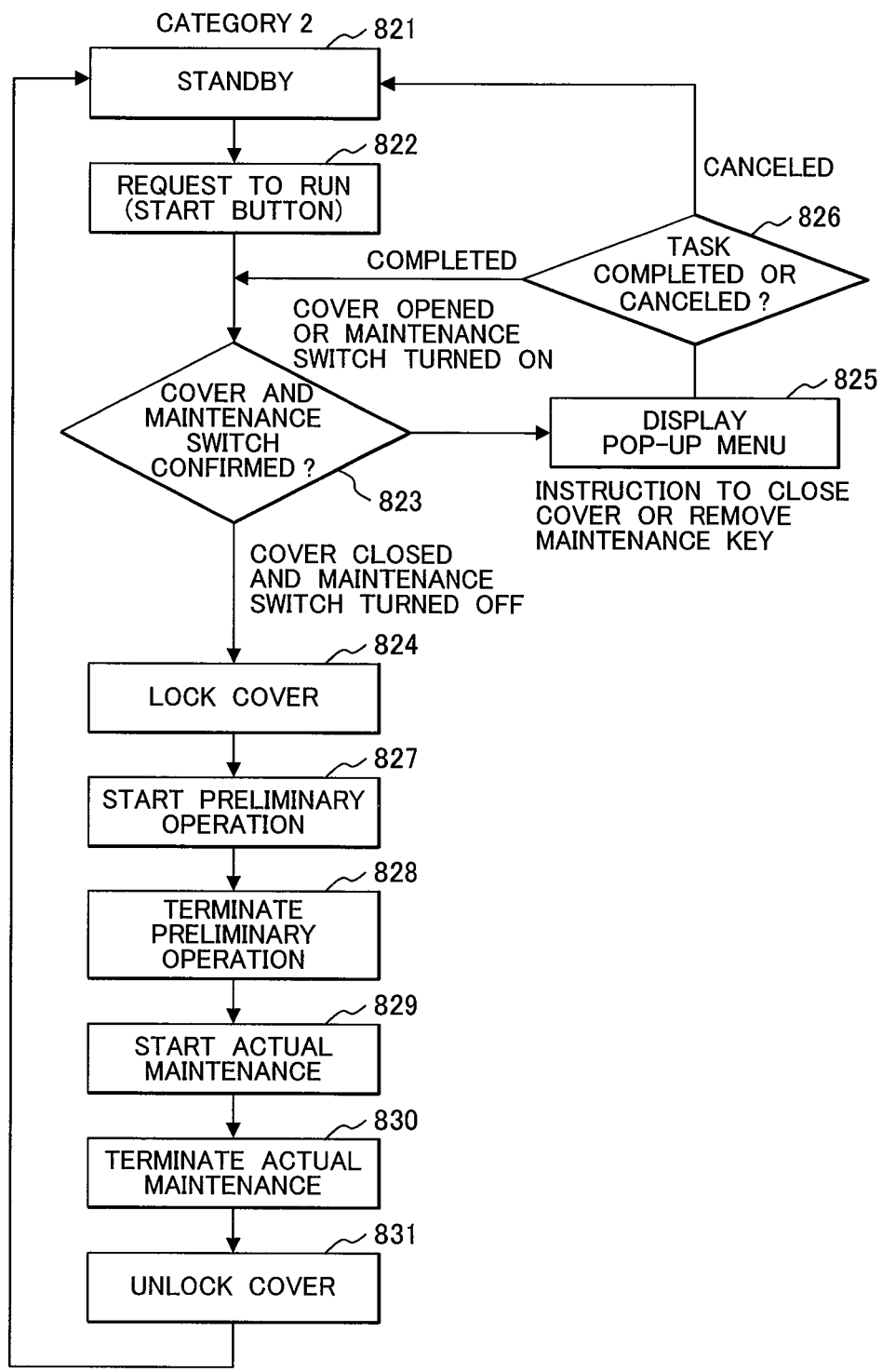
FIG. 8B illustrates a workflow of category 2.

FIG. 8B illustrates a workflow of category 2.

In FIG. 8B, pressing a request start button (822) in the standby state 821 confirms cover opening/closing and the maintenance switch (823). The cover lock state 824 is enabled when the cover is closed and the maintenance switch turns off. The preliminary operation starts (827). The preliminary operation terminates (828). Then, the actual maintenance starts (829). The actual maintenance terminates (830). The cover lock is released (831). Then, the standby state 821 is resumed.

The cover may be opened or the maintenance switch may turn on during the confirmation (823) of cover opening/closing and the maintenance switch. In this case, a pop-up menu appears to close the cover or remove the maintenance key (825). There is provided an option to complete or cancel the task (826). If the task is canceled, the standby state 821 is resumed. If the task is completed, category 2 re-confirms cover opening/closing and the maintenance switch (823).

Category 3 signifies an item in which the preliminary operation accompanies hazardous mechanism operation and the actual maintenance does not accompany hazardous mechanism operation. Category 3 applies to a T/M item that need or need not open the cover during the actual maintenance.

The preliminary operation uses the cover lock mode. The actual maintenance uses the cover lock release mode. In the preliminary operation, the actual maintenance with the cover locked can be assumed safe. Such maintenance can be treated as a normal T/M without the need for a maintenance key. Accordingly, a specific type of maintenance task (hereinafter referred to as a "specific maintenance task") is available without disabling the interlock mechanism.

The user cannot perform the specific maintenance task because of the interlock mechanism. One maintenance task is divided into the preliminary operation and the actual maintenance to be available for the user as category 3 without disabling the interlock mechanism or as category 4 by disabling the interlock mechanism due to the interlock release mechanism.

Figure 8C:
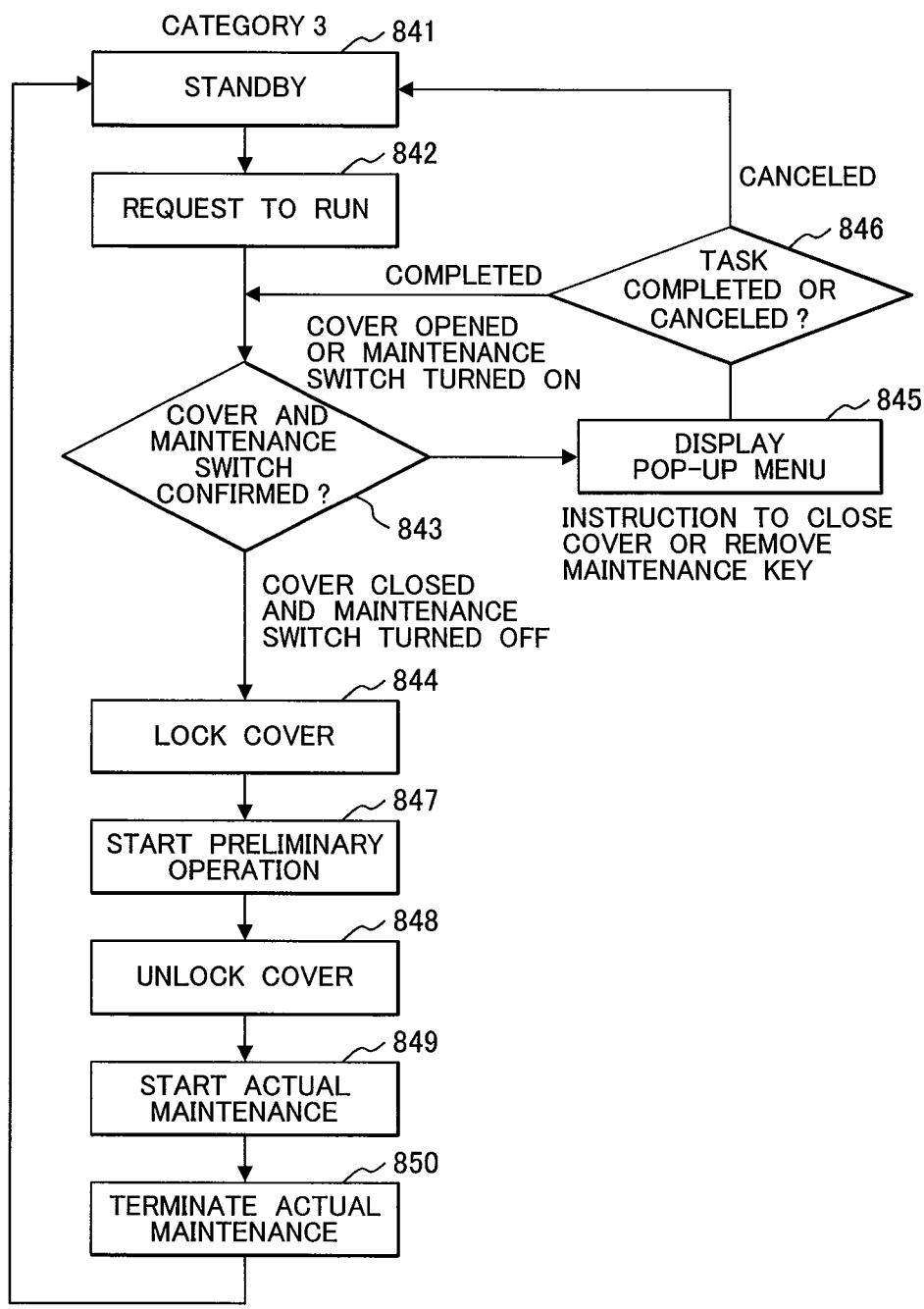
FIG. 8C illustrates a workflow of category 3.

FIG. 8C illustrates a workflow of category 3.

In FIG. 8C, pressing the request start button (842) in the standby state 841 confirms cover opening/closing and the maintenance switch (843). The cover lock state 844 is enabled when the cover is closed and the maintenance switch turns off. The preliminary operation starts (847). The lock is released (848) to start the actual maintenance (849). The actual maintenance terminates (850) to resume the standby state 841.

The cover may be opened or the maintenance switch may turn on during the confirmation (843) of cover opening/closing and the maintenance switch. In this case, a pop-up menu appears to close the cover or remove the maintenance key (845). There is provided an option to complete or cancel the task (846). If the task is canceled, the standby state 841 is resumed. If the task is completed, category 3 re-confirms cover opening/closing and the maintenance switch (843).

Figure 8D:
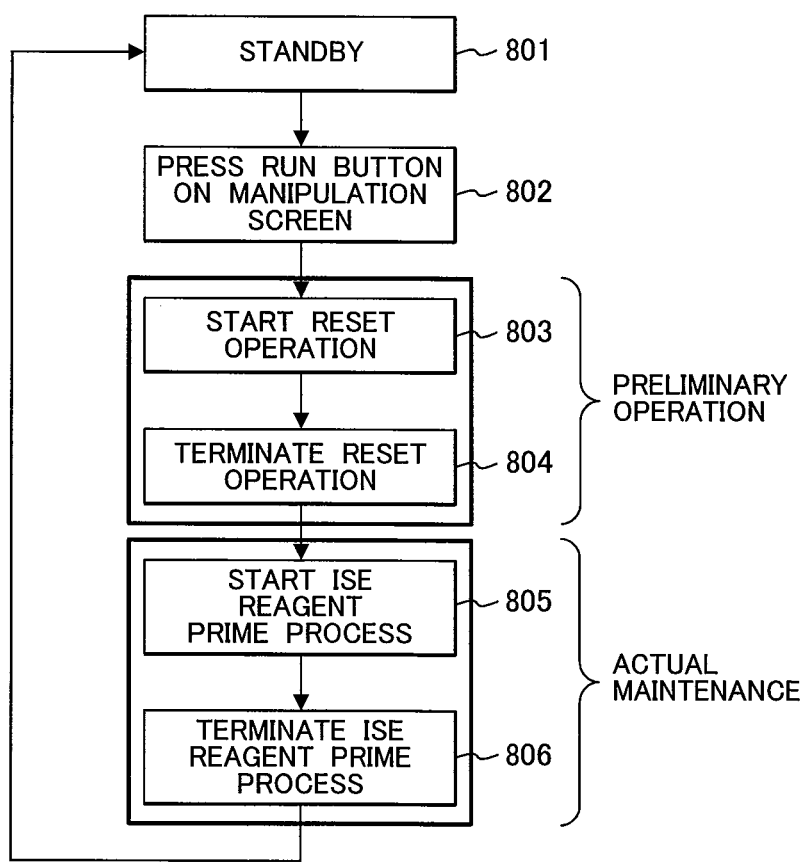
FIG. 8D illustrates a workflow of an ISE reagent prime process as an example of category 3.

FIGS. 8D and 8E illustrate a workflow and an effect of an ISE reagent prime process as an example of category 3.

In FIG. 8D, pressing a run button (802) on the manipulation screen in the standby state 801 starts a reset operation 803. After the reset operation terminates 804, an ISE reagent prime process starts (805). When the ISE reagent prime process terminates (806), the standby state 801 is resumed.

FIG. 8E illustrates cover states during the reset operation and the ISE reagent prime process.

Conventionally, the reset operation and the ISE reagent prime process are assumed to be one operation. However, the example assumes both to be different manipulations and supposes that the reset operation terminates, and then the ISE reagent prime process is performed. According to the example, the cover is locked during the reset operation including operation on a hazard region because opening the cover is hazardous. By contrast, the cover may be opened and unlocked during the ISE reagent prime process because there is no operation on a hazard region.

The solenoid locks the cover only when a hazardous mechanism operates. The cover is unlocked when a hazardous mechanism does not operate. The cover can be opened for visual confirmation during maintenance on even an interlocked device.

Category 4 applies to a T/M item that allows the actual maintenance to accompany hazardous mechanism operation and need or need not open the cover.

Only category 4 is available in the maintenance mode. Category 4 may be replaced by category 2 because the cover may not need to be opened. The system is configured so that the user can select category 2 or 4.

Figure 8F:
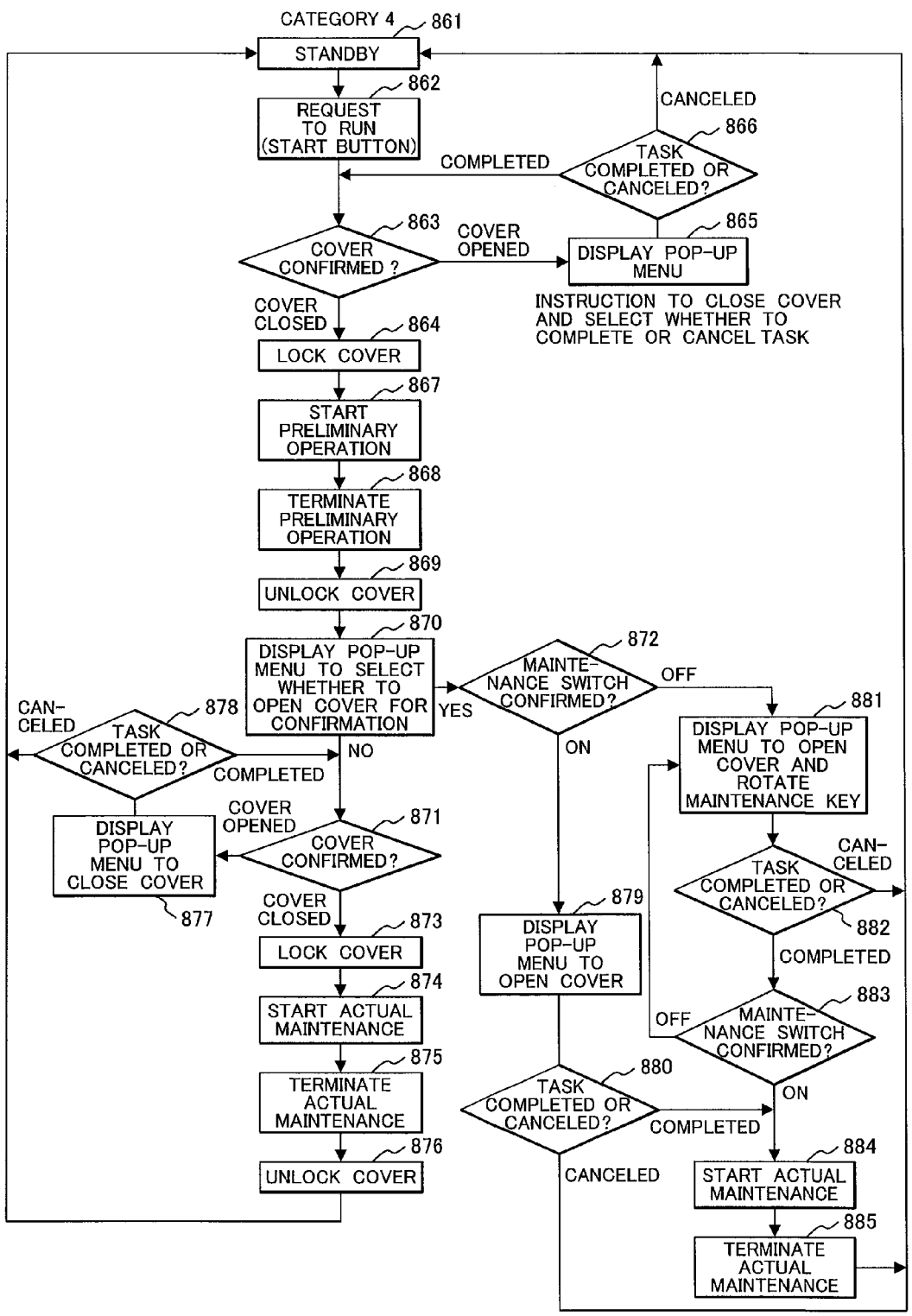
FIG. 8F illustrates a workflow of category 4.

FIG. 8F illustrates a workflow of category 4.

In FIG. 8F, pressing the request start button (862) in the standby state 861 confirms cover opening/closing (863). The cover lock state 864 is enabled when the cover is closed. The preliminary operation starts (867). The preliminary operation terminates (868) and the cover is unlocked (869).

If the cover is opened as a result of the cover opening/closing confirmation (863), a pop-up menu appears to close the cover (865) and determine whether to complete or cancel the task (866). If the task is canceled, the standby state 861 is resumed. If the task is completed, category 4 re-confirms the cover opening/closing (863).

After the cover lock is released (869), a pop-up menu appears to determine whether to open the cover for confirmation (870). If the confirmation is rejected ("No"), category 4 confirms whether the cover is opened or closed (871). If the cover is closed, the cover is locked 873. The actual maintenance starts (874). The actual maintenance terminates (875). The cover is unlocked (876) to resume the standby state 861. If the cover is opened, a pop-up menu appears to close the cover (877) and determine whether to complete or cancel the task (878). If the task is canceled, the standby state 861 is resumed. If the task is completed, category 4 re-confirms the cover opening/closing (871).

If the confirmation is accepted as a result of the selection whether to open the cover for confirmation (870), category 4 confirms whether the maintenance switch turns on or off (872). If the maintenance switch turns on, a pop-up menu appears to open the cover (879) and determine whether to complete or cancel the task (880). If the task is canceled, the standby state 861 is resumed. If the task is completed, the actual maintenance starts (884). The actual maintenance terminates (885). The standby state 861 is resumed.

The maintenance switch may turn off as a result of the confirmation whether the maintenance switch turns on or off (872). In this case, a pop-up menu appears to open the cover and rotate the maintenance key (881) and determine whether to complete or cancel the task (882). If the task is canceled, the standby state 861 is resumed. If the task is completed, category 4 confirms whether the maintenance switch turns on or off (883). If the maintenance switch turns on, the actual maintenance starts (884). When the actual maintenance terminates (885), the standby state 861 is resumed. The maintenance switch may turn off as a result of the confirmation whether the maintenance switch turns on or off (883). In this case, a pop-up menu re-appears to open the cover and rotate the maintenance key (881).

The above-mentioned categories can easily and fast make available a maintenance task that needs to use the maintenance key according to example 1. Decreasing the frequency of using the maintenance key can reduce the hazard and a complicated task of inserting the maintenance key.

Figure 9:
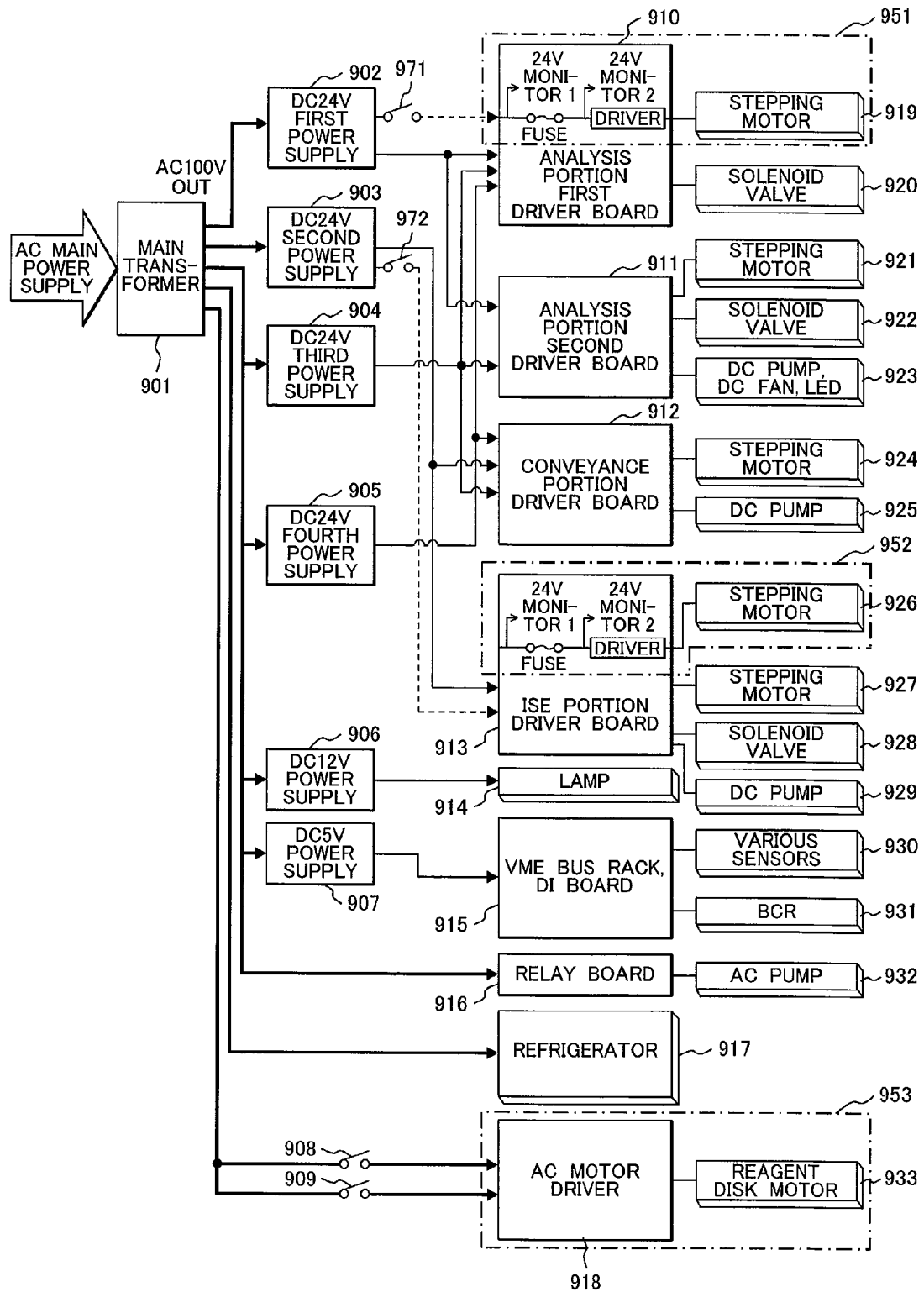
FIG. 9 illustrates a power supply system of the automated analyzer according to the example.

FIG. 9 illustrates a power supply system.

The power supply system in FIG. 9 includes a main transformer 901, a 24 V DC first power supply 902, a 24 V DC second power supply 903, a 24 V DC third power supply 904, a 24 V DC third power supply 905, a 12 V DC power supply 906, a 5 V DC power supply 907, a maintenance switch 908, a safety switch 909, an analysis portion first driver board 910, an analysis portion second driver board 911, a conveyance portion driver board 912, an ISE portion driver board 913, a lamp 914, a VME bus rack 915 (including a VME bus rack and a DI board), a RELAY board 916, a refrigerator 917, an AC motor driver 918, a stepping motor 919, a solenoid valve 920, a stepping motor 921, a solenoid valve 922, a DC pump 923 (including a DC pump, DC fan, and an LED), a stepping motor 924, a DC pump 925, stepping motors 926 and 927, a solenoid valve 928, a DC pump 929, various sensors 930, a BCR 931, an AC pump 932, a reagent disk motor 933, and 24 V DC power relays 971 and 972.

The VME bus complies with one of computer bus standards. The VME bus rack signifies a rack that uses the VME bus. The DI board is an acronym for a Digital In board. The DI board is supplied with digital signals from a sensor or a bar-code reader and transmits signals to the CPU. The RELAY board signifies a relay board (repeating board).

Interlock control targets 951, 952, and 953 correspond to an area enclosed in the dash-dot line. The interlock control target 951 includes part of the analysis portion first driver board 910 and the stepping motor 919. The interlock control target 952 includes part of the ISE portion driver board 913 and the stepping motor 926. The interlock control target 953 includes the AC motor driver 918 and the reagent disk motor 933.

The interlock control targets 951, 952, and 953 allow the interlock release mechanism to disable all or part of the interlock mechanism and enable operation by opening the cover using a means such as the maintenance key. The interlock control targets can remain supplied with the necessary power when the user performs maintenance as needed.

The user can determine whether to perform these operations. The maintenance mode symbol 501 or the lever lock release mode symbol 502 illustrated in FIG. 5 helps the user easily determine availability and unavailability of these operations and improves safety and usability of the device. A manipulation button or a touch panel is used to select these operations.

The reagent disk motor 933 generates large torque. Therefore, the user cannot maintain the reagent disk motor 933 while the normal interlock mechanism functions. According to the example, however, the reagent disk motor 933 is included in the interlock control target 953. The interlock release mechanism works to disable all or part of the interlock mechanism.

According to the example, the stepping motors 919 and 926 can enable only a probe operation.

The device cover opens to turn off the safety switch 909 and turn off the 24 V DC power relays 971 and 972. In this case, the 24 V DC output to the driver boards (analysis portion first driver board 910, analysis portion second driver board 911, conveyance portion driver board 912, and ISE portion driver board 913) stops except a specific power supply system. The driver board uses 24 V DC to control the drive of the stepping motors and operation to open and close the solenoid valves. The interlock disables operation of a specific stepping motor that operates hazardous mechanisms in the analysis portion and the ISE portion. In this case, a related system on the driver board is detected as fused even if it is not actually fused.

To detect blowout of a fuse, the power supply system monitors 24 V DC downstream of the fuse. In addition, the power supply system monitors 24 V DC upstream of the fuse. The power supply system uses the hardware configuration that can accurately detect blowout of the fuse.

Table 4 lists cases in the logic to detect blowout of the fuse.

Table 4 lists fuse states corresponding to combinations of 24 V DC monitors 1 and 2.

TABLE 4

| 24 V monitor 1 | 24 V monitor 2 | Fuse blowout state |
|---|---|---|
| 0 V | 0 V | None |
| 0 V | 24 V | Never |
| 24 V | 0 V | Blown |
| 24 V | 24 V | None |

The driver board is mounted with the DC pump, the DC fan, and the switch contact monitoring circuit that need to be controlled even during interlock operation. These components are supplied with the power of 24 V DC for a different system not contained in the interlock control target. Even a stepping motor without any problem in safety is supplied with the power of 24 V DC for a different system not contained in the interlock control target. Accordingly, category 3 is available during interlock operation, making it possible to drive the circulation pump or monitor various device states.

Similarly, the safety switch 909 at the front of analysis portion stops supplying 100 V AC to the reagent disk that uses an AC motor.

Figure 10:
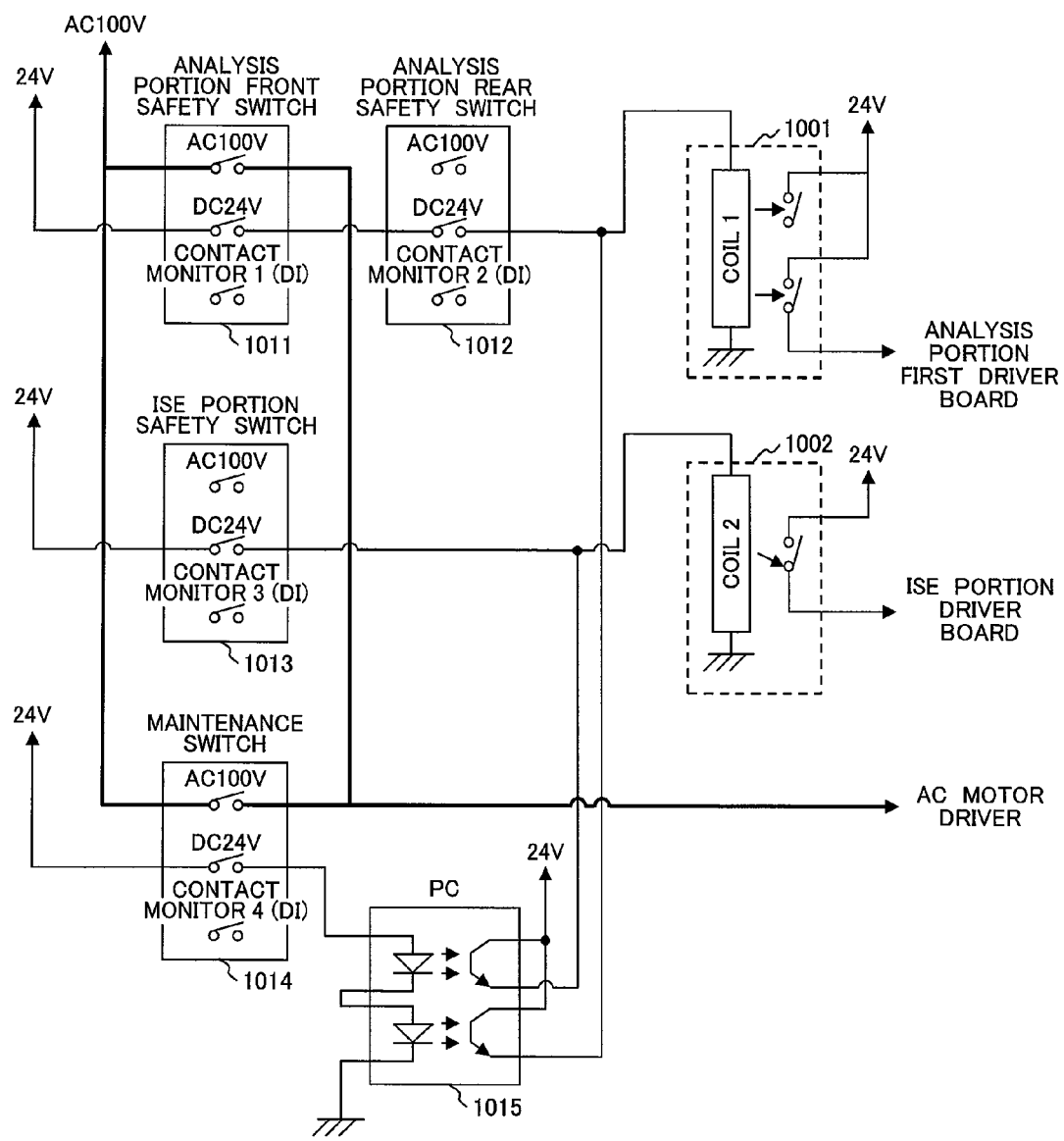
FIG. 10 illustrates a detail view of safety switch circuits and a maintenance switch circuit for FIG. 9.

FIG. 10 illustrates circuits of the safety switch 909 and the maintenance switch 908 in detail.

24 V DC power relays 1001 and 1002 in FIG. 10 are identical to the 24 V DC power relays 971 and 972 in FIG. 9. The availability of power supply using the safety switch 909 in FIG. 9 is electrically divided into the biochemical analysis portion and the ISE portion. That is, the biochemical analysis portion includes an analysis portion front safety switch 1011 and an analysis portion rear safety switch 1012. The ISE portion includes an ISE portion safety switch 1013.

Even opening the cover for the biochemical analysis portion keeps supplying the power to the ISE portion. The opposite is also true. Electrically separating the analysis portion from the ISE portion provides an electric system that is available for other module configurations and is capable of performing T/M on a specific module and performing operation on the other modules.

The maintenance switch 908 in FIG. 9 corresponds to a maintenance switch 1014 in FIG. 10. Power supply to the analysis portion and the ISE portion can be separated by providing a photo coupler 1015 (PC) between the maintenance switch 1014 and a set of coils 1 and 2 for the 24 V DC power relays 1001 and 1002.

The software monitor control will be described.

First, the following describes a case of opening the cover in the standby state.

The standby state is active when the cover is opened. A display on the screen distinguishes this standby state from the other standby state in which the power is supplied. There may be a case of starting an unspecified maintenance operation including operations and initialization. In such a case, an alarm or a pop-up menu is output to notify that the maintenance operation cannot start because the cover is opened. Device states are monitored according to four types of detection situations such as detecting a cover opening sensor, a safety switch contact, driver board fuse blowing, and the maintenance switch contact.

The following then describes transition from the state of opening the cover to the maintenance mode.

When the cover is opened, the use of the maintenance key resumes the power supply of 24 V DC and part of 100 V AC, detects the cover to be open, and does not detect blowing of both fuses on the driver boards. The automated analyzer confirms the maintenance switch detection and transitions to the maintenance mode. Thereafter, the screen displays information so that the user can recognize the maintenance mode. Available maintenance is limited. As illustrated in FIG. 5, maintenance items are marked on the screen so that the user can confirm whether the maintenance items are available.

While there has been described the present invention, the following modifications may be available.

For example, it is known that no hazardous mechanisms operate during post-operation, rack reception mode, or reagent registration. There may be a case where the cover needs to be opened to replace detergent. Only for the purpose of the maintenance, it may be possible to issue an instruction to release the lever lock even not in the standby state. In this case, secure safety needs to be ensured because opening the cover does not stop supplying the power to the related motor or solenoid valve. Further, it may be convenient for users to enable the reagent registration if only a reagent disk cover is closed even not in the maintenance mode to allow covers to open.

Covers may need to cover only portions assumed hazardous, not the entire device. The power need not turn off if a cover to cover non-hazardous portions is opened.

A single screen may display multiple systems when the screen displays available maintenance. There may be a situation where some devices are capable of maintenance. In such a case, a different mark may be displayed.

According to the invention, it is possible to prevent the user from inadvertently touching the mechanism portion including a hazard region during an analysis operation or a maintenance task on the automated analyzer. Only a specific maintenance task can be performed with the device cover opened. In this case, insertion of a maintenance key or a display on the manipulation screen can allow the user to easily recognize that a specific maintenance task is available and the mechanism portion is operating and care must be taken.

The categories according to example 2 can easily and fast make available a maintenance task that needs to use the maintenance key according to example 1. Decreasing the frequency of using the maintenance key can reduce the hazard and a complicated task of inserting the maintenance key.

REFERENCE SIGNS LIST

101 . . . conveyance line,
102 . . . rotor,
103 . . . reagent disk,
104 . . . reaction disk,
105 . . . dispensing mechanism,
106 . . . stirring mechanism,
107 . . . spectroscope,
108 . . . reaction container cleaning mechanism,
109 . . . nozzle cleaning mechanism,
110 . . . specimen container,
111 . . . specimen rack,
112 . . . reaction container,
113 . . . reagent container,
114 . . . shield portion,
115 . . . control unit,
116 . . . nozzle,
117 . . . fluid level sensor,
201 . . . interlock mechanism,
202 . . . top cover,
301 . . . lever,
302 . . . safety switch,
303 . . . maintenance key,
304 . . . solenoid,
401 . . . main transformer,
402 . . . 24 V DC first power supply,
403 . . . 24 V DC second power supply,
404 . . . 24 V DC third power supply,
405 . . . 12 V DC power supply,
406 . . . 5 V DC power supply,
407 . . . DC first power relay,
408 . . . DC second power relay,
409 . . . first driver board,
410 . . . second driver board,
411 . . . lamp,
412 . . . control board,
413 . . . AC drive board,
414 . . . refrigerator,
415, 416 . . . solenoid valve,
417, 418 . . . stepping motor,
419 . . . solenoid valve,
420 . . . DC pump,
421 . . . contact sensor,
422 . . . various sensors,
423 . . . BCR,
424 . . . AC pump,
450 . . . interlock control target,
501 . . . maintenance mode symbol,
502 . . . lever lock release mode symbol,
601 . . . analysis portion front interlock mechanism,
602 . . . analysis portion rear interlock mechanism,
603 . . . ISE portion interlock mechanism,
604 . . . analysis portion front cover,
605 . . . analysis portion rear cover,
606 . . . ISE portion cover,
607 . . . analysis portion hazard region,
608 . . . ISE portion hazard region,
609 . . . maintenance switch,
701 . . . device cover,
702 . . . safety switch,
703 . . . solenoid,
704 . . . maintenance key,
705 . . . maintenance switch, and
720 . . . contact.

The invention claimed is:

1. An automated analyzer comprising:
a conveyance mechanism to convey a specimen;
an analysis portion to analyze the specimen;
a device cover to cover a movable mechanism including the conveyance mechanism;
an interlock mechanism to stop an operation of the movable mechanism when the device cover is opened; and
an interlock release mechanism to disable all or part of the interlock mechanism,
wherein the interlock release mechanism disables the interlock mechanism to enable the operation of the movable mechanism with the device cover opened, and makes a specific maintenance task available which is otherwise disabled by the interlock mechanism.

2. The automated analyzer according to claim 1, further comprising:
a display to visually notify that the device cover is opened, the movable mechanism is inoperative, and only the specific maintenance task is available.

3. The automated analyzer according to claim 2,
wherein the display displays a restriction on an available maintenance task and displays another maintenance task which is available only in a state of activating a maintenance tool, corresponding to whether the interlock mechanism is enabled, partially disabled, or completely disabled.

4. The automated analyzer according to claim 2, further comprising:
a maintenance switch; and
a maintenance key,
wherein the device cover is locked when the device cover is closed after receiving a request to perform maintenance,
wherein a preparatory operation for the maintenance is performed with the device cover locked and the device cover is unlocked thereafter,
wherein a selectable option to open the device cover is displayed, wherein information to open the device cover and rotate the maintenance key is displayed when the option is selected to open the device cover and the maintenance switch opens a contact; and wherein, after confirming that the maintenance switch closes a contact, operation of the movable mechanism is enabled with the device cover opened and the maintenance subsequent to the preparatory operation is performed.

5. The automated analyzer according to claim 1,
wherein all or part of the interlock mechanism is disabled only at a permitted timing.

6. The automated analyzer according to claim 1,
wherein the interlock mechanism locks the device cover when the movable mechanism operates to prevent the device cover from opening, and wherein the interlock mechanism does not lock the device cover and the specific maintenance task is made available without disabling the interlock mechanism when the movable mechanism does not operate.

7. The automated analyzer according to claim 1, further comprising:
a maintenance switch,
wherein the device cover is locked when the device cover is closed and the maintenance switch opens a contact after receiving a request to perform maintenance,
wherein a preparatory operation for the maintenance is performed with the device cover locked and the device cover is unlocked thereafter, and
wherein operation of the movable mechanism is enabled with the device cover opened and the maintenance subsequent to the preparatory operation is performed.

8. A maintenance method for an automated analyzer comprising:
operating a conveyance mechanism to convey a specimen, and an analysis portion to analyze the specimen while a device cover covers a movable mechanism including the conveyance mechanism; and
stopping the operation of the movable mechanism when the device cover is opened by an interlock mechanism; and
enabling the operation of the movable mechanism with the device cover opened by an interlock release mechanism which disables all or part of the interlock mechanism when the device cover is opened,
wherein the interlock release mechanism makes a specific maintenance task available which is otherwise disabled by the interlock mechanism.

9. The maintenance method for the automated analyzer according to claim 8, further comprising:
displaying a visual notification that the device cover is opened, the movable mechanism is inoperative, and only the specific maintenance task is available.

10. The maintenance method for the automated analyzer according to claim 9, further comprising:
displaying a restriction on an available maintenance task and another maintenance task which is available only in a state of activating a maintenance tool corresponding to whether the interlock mechanism is enabled, partially disabled, or completely disabled.

11. The maintenance method for the automated analyzer according to claim 8, wherein
all or part of the interlock mechanism is disabled only at a permitted timing.

12. The maintenance method for the automated analyzer according to claim 8, wherein the interlock mechanism locks the device cover when the movable mechanism operates to prevent the device cover from opening, and
wherein the interlock mechanism does not lock the device cover and the specific maintenance task is made available without disabling the interlock mechanism when the movable mechanism does not operate.

13. An automated analyzer comprising:
a conveyance line to convey a specimen;
a motor to drive the conveyance line;
a device cover which opens and closes to cover the motor and the conveyance line;
an analysis portion including a spectrometer to analyze the specimen;
a mechanical interlock to stop an operation of the motor when the device cover is opened; and
a mechanical interlock release to disable all or part of the mechanical interlock,
wherein the mechanical interlock release disables the mechanical interlock to enable the operation of the motor with the device cover opened, and makes a specific maintenance task available which is otherwise disabled by the mechanical interlock.

14. The automated analyzer according to claim 1, wherein the mechanical interlock stops power to the motor to stop the operation of the motor when the device cover is opened, and
wherein the mechanical interlock release supplies power to the motor to enable the operation of the motor with the device cover opened.

15. The automated analyzer according to claim 13, further comprising:
a display to visually notify that the device cover is opened, the motor is inoperative, and only the specific maintenance task is available.

16. The automated analyzer according to claim 13,
wherein all or part of the mechanical interlock is disabled only at a permitted timing.

17. The automated analyzer according to claim 13,
wherein the mechanical interlock locks the device cover when the motor operates to prevent the device cover from opening, and
wherein the mechanical interlock does not lock the device cover and the specific maintenance task is made available without disabling the mechanical interlock when the motor does not operate.

\* \* \* \* \*